United States Patent [19]
Von Langen et al.

[11] Patent Number: 5,516,779
[45] Date of Patent: May 14, 1996

[54] 17β-SUBSTITUTED-6-AZASTEROID DERIVATIVES USEFUL AS 5α-REDUCTASE INHIBITORS

[75] Inventors: Derek Von Langen, Fanwood; Donald W. Graham, Mountainside; Richard L. Tolman, Warren, all of N.J.

[73] Assignee: Merck & Co., Inc., Rahway, N.J.

[21] Appl. No.: 255,500

[22] Filed: Jun. 8, 1994

[51] Int. Cl.$^6$ ............................................ A61K 31/49
[52] U.S. Cl. ........................... 514/284; 514/253; 546/77; 546/78; 546/61; 544/361
[58] Field of Search ........................... 514/253, 284; 544/361; 546/77, 78, 61

[56] References Cited

U.S. PATENT DOCUMENTS

| | | | |
|---|---|---|---|
| 4,337,584 | 3/1983 | Rasmusson et al. | 546/77 |
| 5,438,061 | 8/1995 | Bergman et al. | 514/284 |

FOREIGN PATENT DOCUMENTS

WO93/13124  8/1993  WIPO.

OTHER PUBLICATIONS

Helliker, Wall St. Jour 7 Jun. 1991, pp. A1, A7.
Stinson, Chem & Eng News 29 Jun. 1992 pp. 7–8.
Diani, Jour Clin, Endo. & Metab. vol. 74 pp. 345–350 (1992).
J. Med. Chem., 6–Azasteroids; Potent Dual Inhibitors of Human Type 1 and 2 Steroid 5–Alpha–Reductase, Frye et al., 1993, vol. 36, 4313–4315.
G. Harris, et al., Pro. Natl. Acad. Sci., vol. 89, pp. 10787–10791, (1992).
C. D. Jones, et al., J. Med. Chem., vol. 36, pp. 421–423 (1993).
G. H. Rusmusson, et al., J. Med. Chem., vol. 29 pp. 2298–2315 (1986).

*Primary Examiner*—Donald G. Daus
*Attorney, Agent, or Firm*—Catherine D. Fitch; Joanne M. Giesser; Melvin Winokur

[57] ABSTRACT

Compounds of the formula

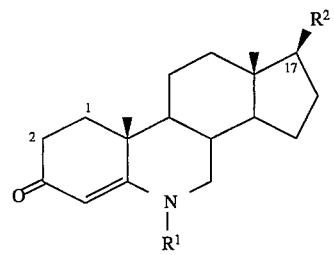

are inhibitors of 5 α-reductase and are useful alone or in combination with other active agents for the treatment of hyperandrogenic disorders such as acne vulgaris, seborrhea, female hirsutism, male pattern baldness, and benign prostatic hyperplasia.

9 Claims, No Drawings

17β-SUBSTITUTED-6-AZASTEROID DERIVATIVES USEFUL AS 5α-REDUCTASE INHIBITORS

FIELD OF THE INVENTION

The present invention provides novel compounds, novel compositions, methods of their use and methods of their manufacture, where such compounds are generally pharmacologically useful as agents in therapies whose mechanism of action rely on the inhibition of reductase, and more particularly, the inhibition of 5α-reductase isozyme type 1.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neff, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g., the prostate, is 5α-dihydrotestosterone ("DHT"), formed locally in the target organ by the action of 5α-reductase, which converts testosterone to DHT. Inhibitors of 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et all., Proc. Natl. Acad. Sci. USA, Vol. 89, pp. 10787–10791 (Nov. 1992). The isozyme that principally interacts in skin tissues is conventionally designated as 5α-reductase 1 (or 5α-reductase type 1 ), while the isozyme that principally interacts within the prostatic tissues is designated as 5α-reductase 2 (or 5α-reductase type 2).

Since 5α-reductase type 1 and type 2 convert testosterone to DHT, inhibition of either or both of the isozymes would serve to alleviate the conditions and diseases mediated by DHT. The present invention addresses this by providing novel compounds that are active as inhibitors of 5α-reductase type 1.

SUMMARY OF THE INVENTION

The novel compounds of the present invention are those of structural formula I:

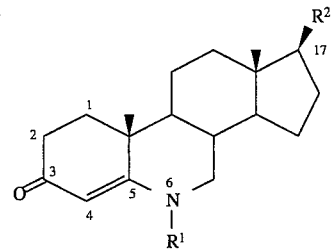

or a pharmaceutically acceptable salt or ester thereof, and are inhibitors of 5α-reductase, particularly 5α-reductase type 1. The compounds of formula I are useful in the oral, systemic, parenteral or topical treatment of hyperandrogenic conditions such as acne vulgaris, seborrhea, androgenic alopecia which includes female and male pattern baldness, female hirsutism, benign prostatic hyperplasia, and the treatment of prostatic carcinoma, as well as in the treatment of prostatitis.

Therefore it is an object of this invention to provide compounds that have sufficient activity in the inhibition of 5α-reductase type 1. It is an additional object of this invention to provide methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis. It is a further object of this invention to provide pharmaceutical compositions for the compounds of formula I. Another object of this invention is to provide compounds of formula I in combination with other active agents, for example a 5α-reductase type 2 inhibitor, such as finasteride, or a potassium channel opener, such as minoxidil, or a retinoic acid or a derivative thereof, or an α1- or α1$_c$-adrenergic receptor antagonist, or combinations of such other active agents with a compound of formula I, wherein such combinations would be useful in one or more of the above-mentioned methods of treatment or pharmaceutical compositions.

DETAILED DESCRIPTION OF THE INVENTION

The novel compounds of this invention have the structural formula I:

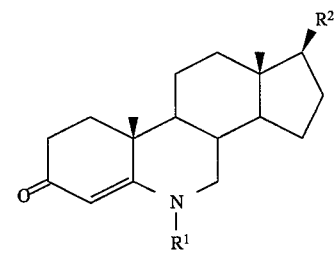

or a pharmaceutically acceptable salt or ester thereof, wherein:
 $R^1$ is selected from -H,-CH$_3$ and-CH$_2$CH$_3$;
 $R^2$ is selected from:
 1) -H, -OH, -NH2, or =O,
 2) -C$_{1-12}$ alkyl,
 3) -C$_{1-12}$ alkyl-phenyl,
 4) -O-C$_{1-12}$ alkyl or-S(O)n-C$_{1-12}$ alkyl, 5) -O-Het or -S(O)$_n$-Het,
6) -O-phenyl or-S(O)$_n$-phenyl,
7) -C$_{1-6}$ alkyl-X-C$_{1-12}$ alkyl,
8) -C$_{1-6}$ alkyl-X-Het,
9) -C(O)-phenyl,
10) -X-C(O)-C$_{1-12}$ alkyl,
11 ) -OC(O)-NHC$_{1-12}$ alkyl,
12) -OC(O)-NH-phenyl,
13 ) -CN, and
14) -NR$^3$R$^4$, wherein R$^3$ and R$^4$ are each independently selected from -H, C$_{1-12}$ alkyl, phenyl and Het;

Het is selected from piperidinyl, piperazinyl, pyrrolidinyl, pyrrolyl, furanyl and thienyl;

X is selected from the group consisting of O, NH and S(O)$_n$; and n is zero, 1 or 2.

Combinations of substituents and/or variables are permissible only if such combinations result in stable compounds.

In one embodiment of the instant invention are compounds of formula I wherein X is selected from O and S.

In another embodiment of the instant invention are compounds of formula I wherein:

R$^1$ is selected from -H and -CH$_3$; and

R$^2$ is selected from -H,-OH, -O-C$_{1-12}$ alkyl, -C$_{1-12}$ alkyl-phenyl, -O-C$_{1-12}$ alkyl, -O-phenyl, -OC(O)-NHC$_{1-12}$ alkyl, -S(O)$_n$-C$_{1-12}$alkyl, and -S(O)$_n$-phenyl.

In one class of this embodiment are compounds further limited to those wherein:

R$^1$ is selected from -H and -CH$_3$;

R$^2$ is selected from -H,-OH,=O,-C$_{1-12}$ alkyl,-O-C$_{1-12}$ alkyl, -OC(O)-NHC$_{1-12}$ alkyl and -S(O)$_n$-C$_{1-12}$ alkyl.

Examples of compounds within this class include, but are not limited to, the following:

6-methyl-6-aza-androst-4-en-3,17-dione (VII);
6-methyl- 17-propyl-6-aza-androst-4-en-3-one (X);
6-methyl-6-aza-androst-4-en-3-one (XII);
6-methyl-17-hydroxy-6-aza-androst-4-en-3-one (XIII);
6-methyl- 17-t-butylcarbamoyloxy-6-aza-androst-4-en-3-one (XIV);
6-aza-cholest-4-en-3-one (XV); and
6-methyl-6-aza-cholest-4-en-3-one (XVI).

The term "Δ4" indicates a double bond at the C4-C5 position, and as such may be used throughout this application. For example, the name "6-methyl-6-aza-androst-4-en-3,17-dione" and "A4-6 -methyl-6-aza-androsten-3,17-dione" both refer to the same structural compound.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc. "Alkyloxy" (or "alkoxy") represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like.

The heterocyclic ring represented by the term "Het" may be attached to structural formula I at any heteroatom (N, O or S) or carbon atom in the ting which results in the creation of a stable structure.

Also included within the scope of this invention are pharmaceutically acceptable salts of the compounds of formula I, where a basic or acidic group is present on the structure. Where a basic group is present, such as amino, an acidic salt, i.e., hydrochloride, hydrobromide, acetate, pamoate, and the like, can be used as the dosage form.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, and valerate.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" means that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating hyperandrogenic conditions including androgenic alopecia, male pattern baldness, acne vulgaris, seborrhea, and female hirsutism by oral, systemic, parenteral or topical administration of the novel compounds of formula I either alone or in combination with a 5α-reductase 2 inhibitor, or a potassium channel opener, or a retinoic acid or derivative thereof. Alternatively, treatment may encompass administration of a combination of a compound of formula I with a 5α-reductase 2 inhibitor and another active agent such as a potassium channel opener, or a retinoic acid or derivative therof. The term "treating androgenic alopecia" is intended to include the arresting and/or reversing of androgenic alopecia, and the promotion of hair growth.

The present invention has the further objective of providing methods of treating benign prostatic hyperplasia, prostatitis, and treating prostatic carcinoma by oral, systemic or parenteral administration of the novel compounds of formula I either alone or in combination with a 5α-reductase 2 inhibitor. Alternatively, treatment may encompass administration of a combination of a compound of formula I with a 5α-reductase 2 inhibitor and another active agent such as an α1 or an α1$_c$ adrenergic receptor antagonist.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The daily dosage of the products may be varied over a range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of androgenic alopecia, male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of acne vulgaris, androgenic alopecia, male pattern baldness, seborrhea, female hirsutism, benign prostatic hyperplasia, prostatitis and the treatment of prostatic cancer, the compounds of the instant invention can be combined with a therapeutically effective mount of another 5α-reductase inhibitor, such as finasteride, or other 5α-reductase inhibitor compounds having type 2 activity or dual activity for both isozymes, in a single oral, systemic, or parenteral pharmaceutical dosage formulation. Alteratively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective mount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride, or a type 1 and type 2 dual inhibitor, in combination with a compound of the present invention and a potassium channel opener such as minoxidil. The active agents can be administered in a single topical dosage formulation, or each active agent can be administered .in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published 20 February, 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g., an ester or amide derivative thereof, such as e.g., tretinoin or isotretinoin. Optionally, this combined therapy for acne vulgaris may further include a 5α-reductase type 2 inhibitor such as finasteride, or a dual type 1 and type 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-$1_c$ adrenergic receptor antagonist. Compounds which are useful as alpha-1 c adrenergic receptor antagonists can be identified according to the procedures described in PCT/US93/09187 (WO94/08040, published April, 14, 1994).

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carders (collectively referred to herein as "carder" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carder such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

SCHEME I

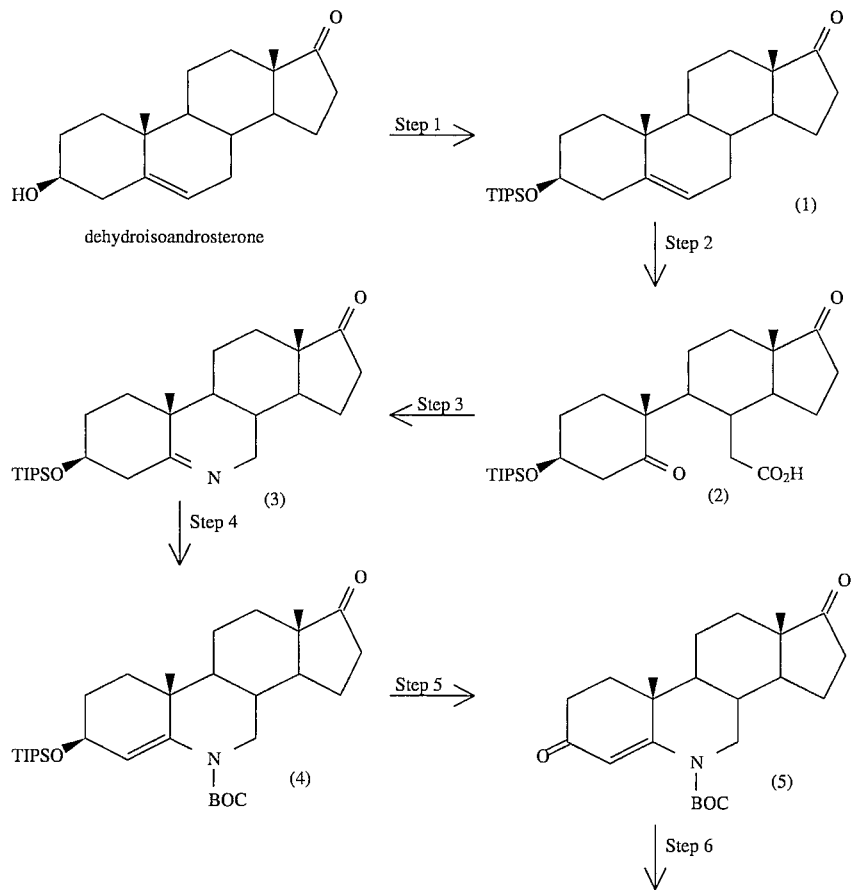

-continued
SCHEME I

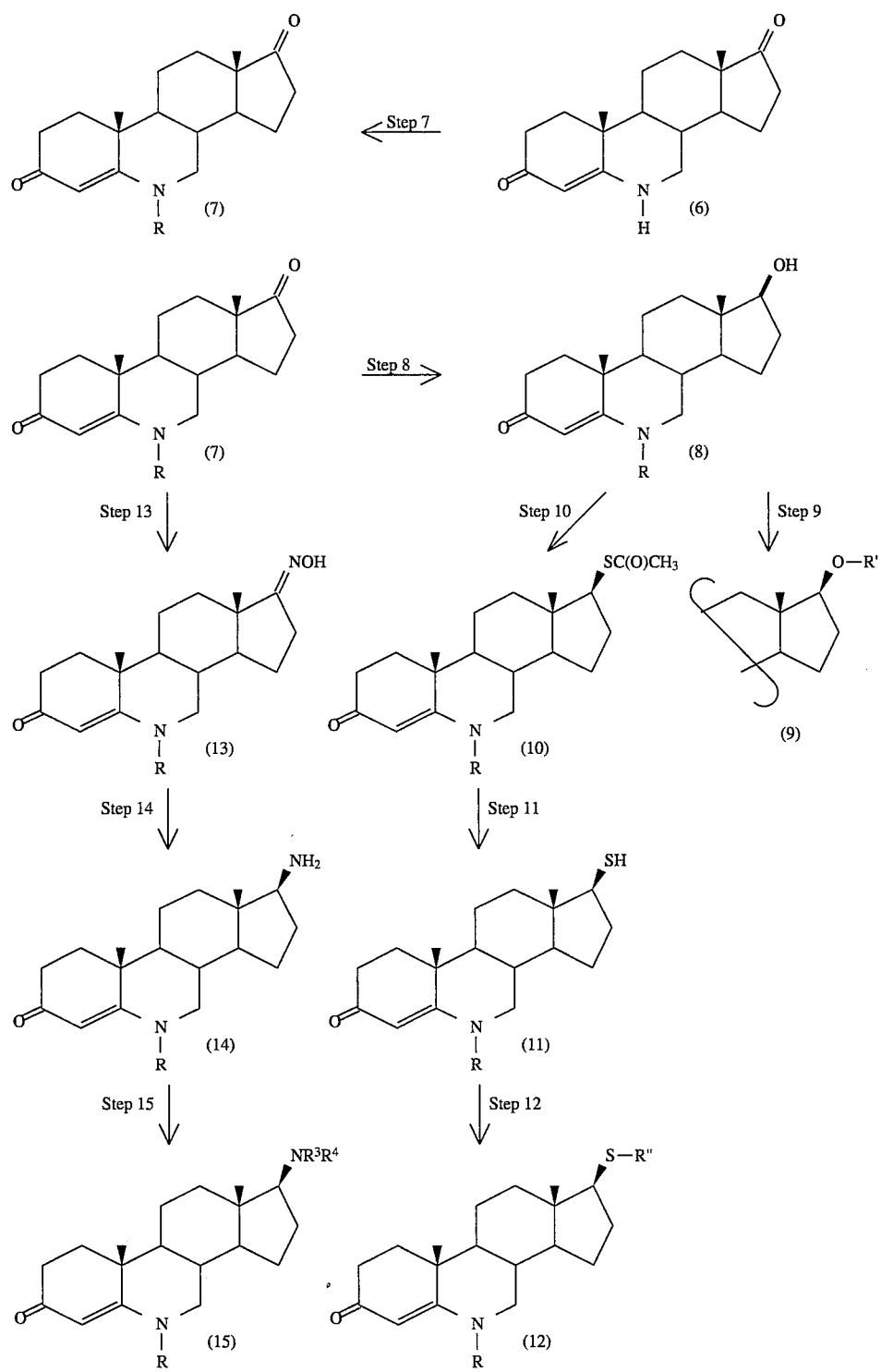

The compounds of this invention can be prepared as shown in Scheme 1. Dehydroisoandrosterone is commercially available, e.g., from Sigma Chemical Co. Steps 1–6 are described in the Examples.

In Step 1, the 3-hydroxyl functionality is protected, preferably with a triisopropylsilyl (TIPS) group employing standard conditions using, e.g., TIPSOTf/lutidine or TIP-SCl/imidazole.

In Step 2 the 5-olefin is oxidatively cleaved to yield the keto-acid 2. This is accomplished in a multi-step sequence by (a) dissolving the olefin in a dichloromethhane/methanol solution at low temperature and saturating with ozone gas, (b) reductive work-up of the ozonide with dimethylsulfide or zinc/acetic acid, and (c) oxidation of the keto aldehyde using chromium trioxide, e.g., $CrO_3$/HOAc or $CrO_3$/$H_2SO_4$ (Jones reagent, also known as Fieser's reagent; see Fieser, L.F., J.

Am. Chem. Soc., vol 70, 3237 (1948)) to yield the keto-acid. Alteratively, the oxidation of the keto aldehyde may be done using $NaClO_2/NH_2SO_3H/NaH_2PO_4$ in aq. THF to yield the keto-acid (see Lindgren, B.O., Acta Chem. Scand, vol 27, 888 (1973))

In Step 3, ring closure is effected in another multi-step sequence by (a) forming the acid chloride of the keto-acid 2 using oxalyl chloride or thionyl chloride, (b) formation of the acylazide by treating the acid chloride with sodium azide, (c) thermal rearrangement of the acyl azide to the isocyanate by heating in a suitable solvent such as toluene and finally (d) ring closure under basic or acidic conditions to give the imine 3.

In Step 4, the nitrogen is protected with a BOC (t-butoxycarbonyl) group which causes migraton of the olefin to the 4 position of the steroid using standard conditions such as BOC anhydride/pyridine.

In Step 5, the silyl protecting group is removed with a fluoride reagent such as TBAF (tetrabutylammonium fluoride) to give the 3-OH which can be oxidized in a number of ways, e.g., using Jones reagent, TPAP (tetrapropylammonium perruthenate), or PDC (pyridinium dichromate), to give the vinylogous amide 5.

In Step 6, the nitrogen is deprotected under acidic conditions to yield the unprotected primary amide 6. Alteratively, the sequence can proceed using the 4-NBOC compound 5.

In Step 7, the secondary vinylogous amide 6 is alkylated using standard techniques known to those of ordinary skill in the art, for example using base such as sodium hydride and an alkylating agent such as MeI or EtI using either THF or DMF as a solvent, to give the tertiary vinylogous amide 7 wherein R 1 is methyl or ethyl.

In Step 8, the ketone 7 is reduced with a suitable hydride source, usually sodium borohydride in ethanol to give the alcohol 8. In Step 9, the alkoxide can be generated from alcohol 8 with a base such as sodium hydride, and alkylated with a commercially available alkyl iodide to give the ether c, (R'=alkyl). The alcohol 8 can also be reacted with a fluorinated heterocycle to yield the heterocyclic ethers (R'= Het) or with a fluorinated aryl compound to give the aryl ethers (R'=Ph). Syntheses for 17-aryl, -heterocyclic and-alkyl ethers are also described, e.g., in WO 93/04746. Alternatively, the alcohol 8 can be reacted with commercially available acid chlorides to give esters 9 (R'=C(O)-alkyl). The alcohol 8 can also be reacted with an isocyanate (RNCO, where R is alkyl or aryl) to give carbamates 2 (R'=C(O)-NHR), for example phenylisocyanate to give the phenylcarbamate (R'=C(O)-NH-Ph).

In Step 10 the alcohol 8 is converted to the thioacetic acid 10 via a Mitsunobo reaction (Mitsunobo, Synthesis, vol. 1, 1, 1981 ). Alternativly, other thio-acids can be utilized to give thio-esters of the type 10. The thio ester is hydrolyzed in Step 11 under basic aqueous conditions to give the thiol 11. Finally, in Step 12, the thiol is alkylated as were the alcohol examples in Step 9, to give the thio ethers 12 (R"=alkyl, Het or Ph). The thiol 11 can also be reacted with commercially available acid chlorides to give thioesters (R"=-C(O)-alkyl).

In Step 13, the ketone 7 is treated with hydroxyl amine to yield the 17-oxime 13. In Step 14, the oxime is reduced using platinum catalyst and hydrogen to yield the free amine 14 which, in Step 15, can be alkylated using sodium hydride and the desired alkyl iodide, Het iodide or phenyl iodide to provide 15. This alkylation can be performed once to yield the secondary amine or twice to give a tertiary amine. Alternatively, the free amine 14 can be reacted with a commercially available acid chloride to yield the 17-amides.

SCHEME II

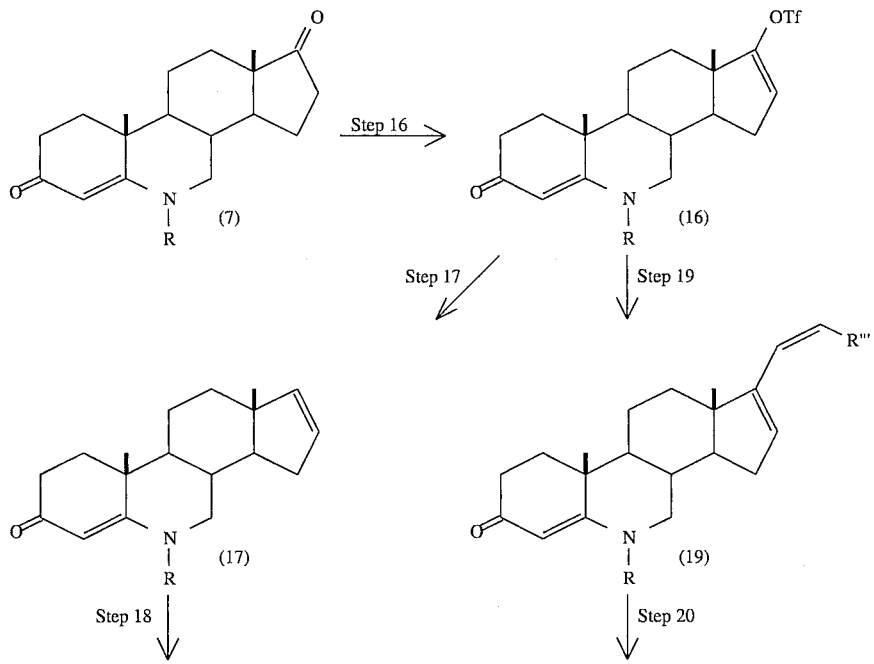

-continued
SCHEME II

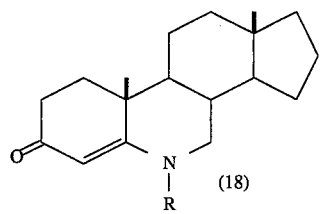 (18)

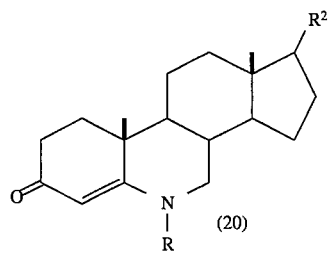 (20)

In Scheme II, Step 16, the ketone 7 is converted to its triflate 16 by quenching the potassium enolate with a suitable triflating reagent, such as N-phenytrifluoromethanesulfonimide. In Step 17, the triflate 16 can be converted to the Δ16 compound 17 using tributyltin hydride and a palladium catalyst. Step 18 is the catalytic hydrogenation of the olefin 17 to the saturated compound 18.

Alternatively, the triflate 16 can be reacted with an alkyltributyl tin compound using a palladium catalyst to yield an unsaturated compound such as 19 where R'''= hydrogen, alkyl, alkaryl, $C_{1-12}$alkyl-X-alkyl, or $C_{1-12}$alkyl-X-Het. Many alkyltributyl tin compounds are commercially available or can be synthesized according to standard techniques in the art; see, e.g., Stille, J., J. Am. Chem. Soc., Vol. 108, 3033 (1986). Some examples of alkyltributyl tin compounds include vinyltributyltin, phenyltrimethyltin, benzyltrimethyltin, tetrabutyltin and allyltributyltin.

In Step 20, the compound is saturated using hydrogen and a suitable catalyst such as Pd/C, Pt/C or when aryl groups are present Rh/C to yield the final product 20 ($R^2$- alkyl, alkyl-Ph).

SCHEME III

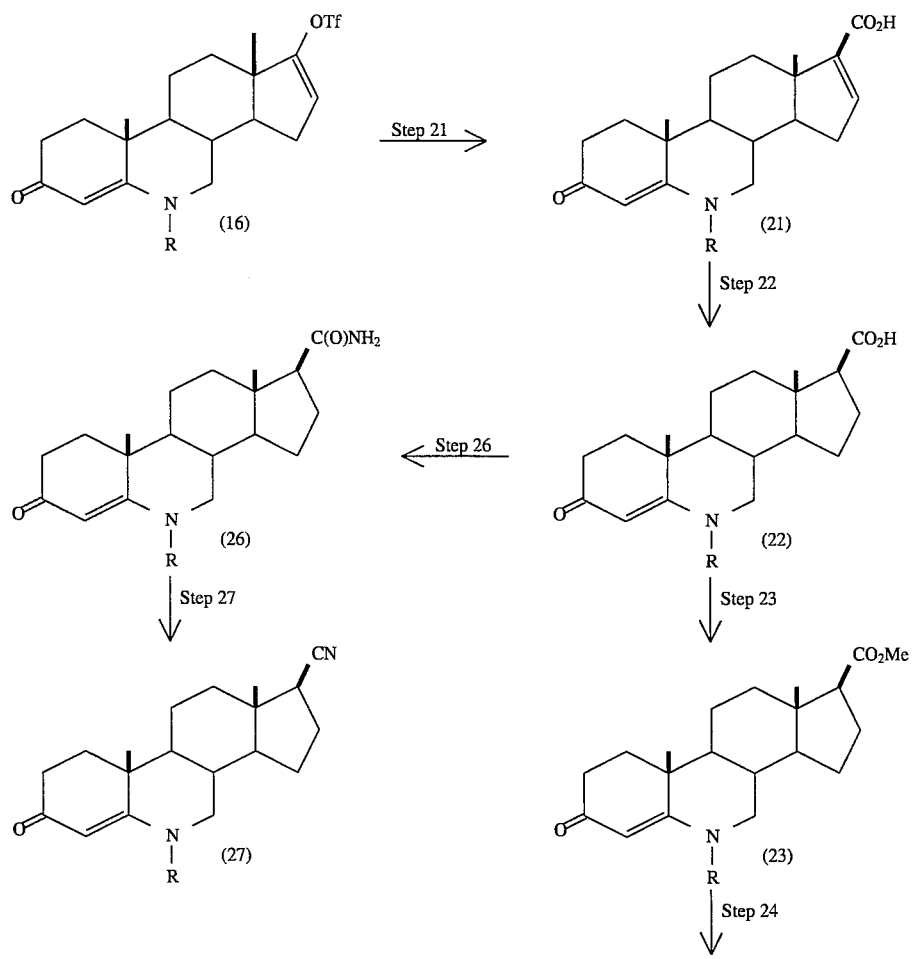

-continued
SCHEME III

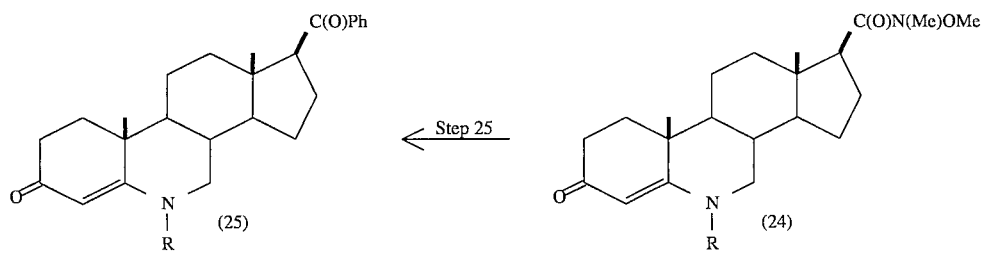

As shown in Scheme III, Step 21, the triflate 16 can be treated with a palladium catalyst and triethylammonium formate in an atmosphere of carbon monoxide to yield the acid 21. The acid can be saturated with hydrogen and a suitable catalyst such as palladium on carbon to yield acid 22.

In Step 23, the acid is esterified to the methyl ester 23 which is then convened in Step 24 to the Weinreb amide 24 (Weinreb, S., Tetrahedron Lett., vol. 22, 3815, (1981)). In Step 25, the amide 24 is treated with phenyl Grignard reagent to yield the phenyl ketone 25.

In Step 26, the acid 22 is convened to its primary amide 26 employing standard coupling conditions, e.g., using a reagent such as DCC (1,3-dicyclohexylcarbodiimide). The amide 26 is then dehydrated using a dehydrating reagent such as phosphourous pentoxide to give the nitrile 27.

For compounds with a sulfur containing substituent, the sulfur can be oxidized to the sulfoxide or sulfone using standard techniques known in the art, e.g., with MCPBA (3-chloroperoxybenzoic acid) or OXONE® (potassium peroxymonosulfate). For example, the sulfoxide can be formed by using about one molar equivalent of MCPBA at about 0° C., while the sulfone can be formed by using about two molar equivalents of MCPBA at a higher temperature, e.g., at room temperature.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius. 1H and 13C nuclear magnetic resonance (NMR) spectra were taken at 400 or 500 MHz at ambient temperature in the solvents indicated. Some abbreviations used herein are as follows: "BOC" is t-butoxycarbonyl; "BOC anhydride" is di-t-butyl dicarbonate $\{O(CO2C(CH_3)_3)_2\}$; "DBU" is 1,8-diaza-bicyclo[5.4,0] undec-7-ene; "DMS" is methyl sulfide $\{(CH_3)_2S\}$; "DMF" is dimethylformamide; "EtOAc" is ethyl acetate; "IPA" is isopropyl acetate; "PDC" is pyridinium dichromate; "Ph" is phenyl; "TBAF" is tetrabutylammoniumfluoride; "TBDMS" is t-butyldimethylsilyl; "Tf" is -$SO_2CF_3$; "TFA" is trifluoroacetic acid; "THF" is tetrahydrofuran; "TIPS" is triisopropylsilyl; "TIPSO" is triisopropylsilyloxy. Potassium hexamethyldisilazide (KHMDS) is also known as potassium bis(trimethylsilyl)amide.

SCHEME IV

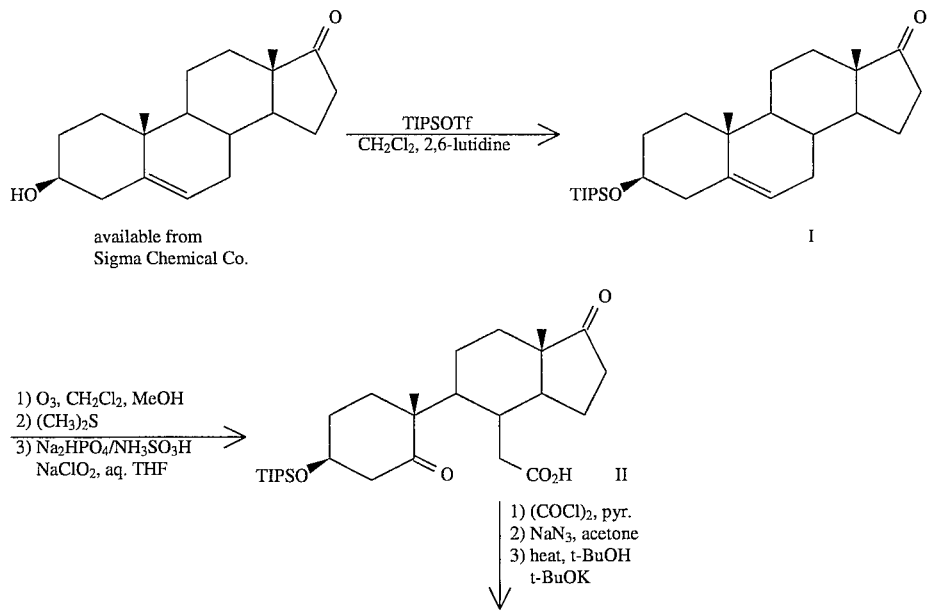

-continued
SCHEME IV

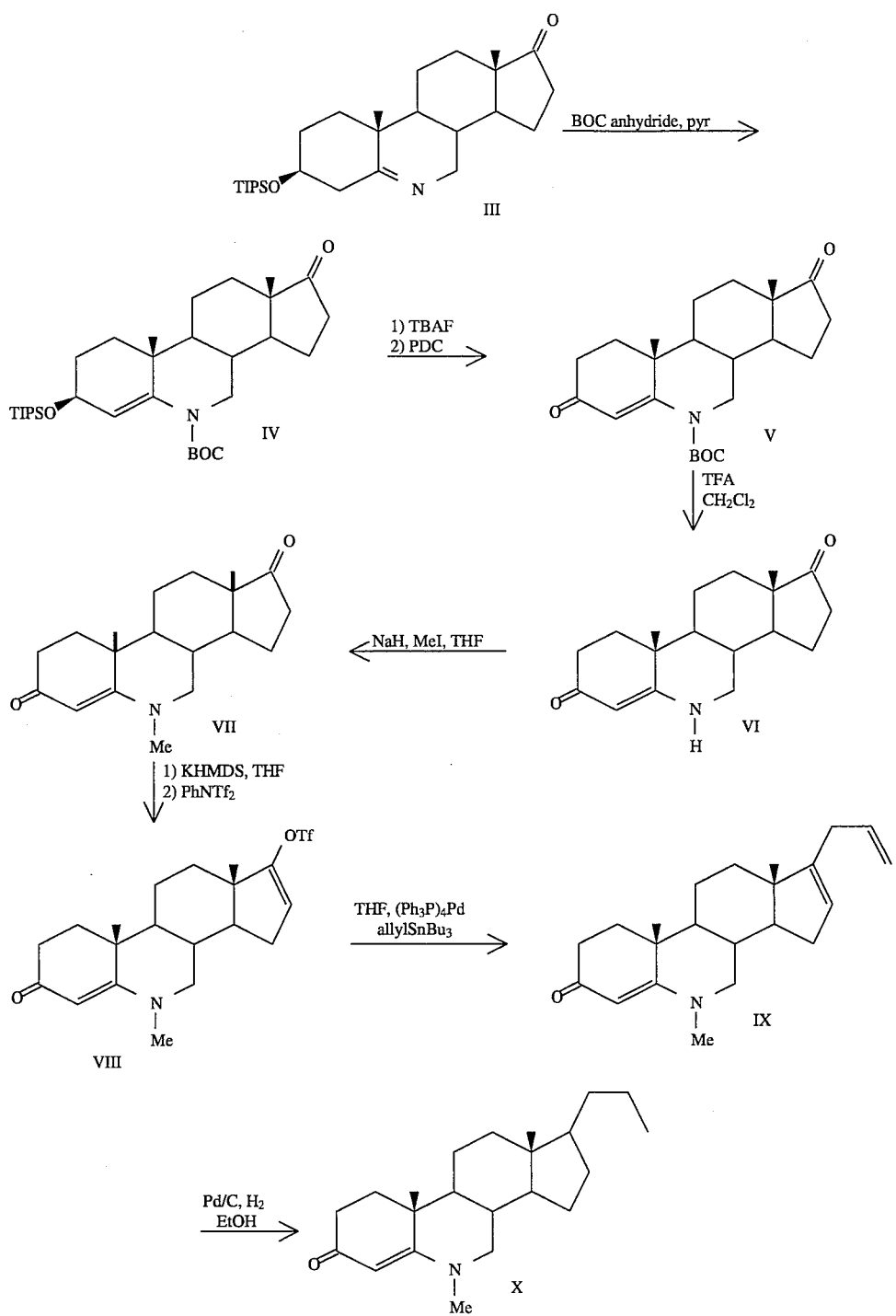

EXAMPLE 1

Preparation of 3β-triisopropylsilyloxy -Δ⁵-androstan-17-one (I)

To a solution of dehydroisoandrosterone (12 g, 41.6 mmol, Sigma Chemical Co.) in DMF (60 mL) was added imidazole (5.6 g, 2 eq) and triisopropylsilylchloride (16 mL, 1.8 eq). After stirring overnight the solution was diluted with dichloromethane (25 mL) and washed with 1N HCl, 1N NaHCO$_3$, water and brine. The solution was dried over magnesium sulfate, filtered and concentrated yielded a waxy solid. Chromatography (silica gel, Hexane:EtOAc 10:1) yielded 3β-triisopropylsilyloxy-Δ⁵-androstan-17-one as a colorless solid. ¹H NMR (CDCl$_3$): 5.35 (vinyl H); 3.55 (3αH); 1.05, 0.90 (18,19 Me).

EXAMPLE 2

Preparation of 3β-triisopropylsilyloxy-$\Delta^5$-6-aza-androsten-17-one (III)

Step A:

A solution of 3β-triisopropylsilyloxy-$\Delta$5-androstan-17-one (I) (17 g) in methanol (150 mL) and dichloromethane (300 mL) was chilled to −78° C. and gassed with ozone until a blue color persisted. Nitrogen was then bubbled through the solution to dissipate the excess ozone and the reaction Solution treated with methyl sulfide (17 mL, excess), removed from the cold bath and let stand at room temperature for 1 hour. The reaction was then concentrated to yield a thick oil.

Step B:

The keto-aldehyde from part A was taken into THF (90 mL) treated with 2.7M $Na_2HPO_4$ (22.5 mL) and 1M $NH_3SO_3H$ (53 mL) and cooled to 0° C. Dropwise addition of 1M NaClO2 (57 mL) caused the reaction solution to become bright yellow colored and the reaction stirred 1 hr at 0° C. The reaction was diluted with EtOAc and washed with water and brine, dried over magnesium sulfate filtered and concentrated to give a colorless oil (19 g). The oil was chromatographed (silica gel, 20%–50% EtOAc/Hexanes) to yield keto-acid (II).

Step C:

The keto-acid (ID (9.5 g) was dissolved in ether (150 mL) and DMF (12 mL). The reaction was treated with thionyl chloride (10 mL) and stirred at ambient temperature for 30 min. The yellow solution was poured into ice water (250 mL) and then extracted with ether. Drying over magnesium sulfate, filtration and removal of solvent gave a yellow solid. This solid was taken into acetone (120 mL) and treated with sodium azide (2.6 g in 26 mL water). After stirring at room temperature for 30 min. the reaction was diluted with water, and extracted with ether. The ether solution was washed with water, dried, filtered and concentrated to yield the acyl-azide as a brown syrup. IR (CHCl3) 2138 $cm^{-1}$.

Step D:

The acyl azide (8.6 g) from part C was taken into toluene (80 mL) and refluxed for 20 min. cooled to room temperature and concentrated to a dark oil. The oil was taken into t-butanol (150 mL) and potassium t-butoxide (1 g) was added. The resulting mixture was warmed to reflux for 20 min. then cooled. The reaction was diluted with ether, washed with water, then brine, dried and concentrated to yield a dark oil. The oil was chromatographed (silica gel, 15%-50% EtOAc/Hexanes) to yield 3β-triisopropylsilyloxy-$\Delta^5$-6-aza-androsten-17-one (III). $^1$H NMR ($CDCl_3$): 3.65 (3αH); 1.09, 1.05 (18,19 Me); $^{13}$C NMR ($CDCl_3$) 173.8 (C17); 54.2 (C5).

EXAMPLE 3

Preparation of 3β-triisopropylsilyloxy-$\Delta^4$-6-t-butylcarboxy-6-aza-androsten-17-one (IV)

A solution of 3β-triisopropylsilyloxy-$\Delta^5$-6-aza-androsten-17-one (III, 8 g) and pyridine (30 mL) was treated with di-t-butyl dicarbonate (8.5 g) and the resulting solution stirred overnight. The solution was concentrated to a brown oil which was purified by chromatography (silica gel, Hexanes:EtOAc 3:1) to give 3β-triisopropylsilyloxy-$\Delta^4$-6-t-butylcarboxy-6-aza-androsten-17-one (IV) as a viscous amber oil. $^1$H NMR ($CDCl_3$): 5.41 (vinyl H); 4.38 (3αH); 1.45,1.56 (t-BOC rotamers); 1.1 (TIPS Me); 1.11,0.92 (18,19 Me).

EXAMPLE 4

Preparation of $\Delta^4$-6-t-butylcarboxy-6-aza-androsten-3,17-dione (V)

A solution of 3β-triisopropylsilyloxy-$\Delta^4$-6-t-butylcarboxy-6-aza-androsten-17-one (3.5 g) and tetrabutylammoniumfluoride (20 mL, 1M in THF) was heated at reflux for 15 min. The reaction was cooled, concentrated and taken into EtOAc, and washed with water, brine, dried over anhydrous sodium sulfate, filtered and concentrated to afford an amber oil. The oil was taken into DMF (60 mL) and PDC (9.5 g) was added. The mixture was heated to 75° C. for 2 hours then poured into ice water (100 mL). This solution was extracted with EtOAc (x3) and the combined organics washed with a 5% copper sulfate solution and brine. Drying with magnesium sulfate, filtration and removal of volatiles gave an amber oil. Chromatography (silica gel, Hexanes:EtOAc 2:1 ) gave $\Delta^4$-6-t-butylcarboxy-6-aza-androsten-3,17-dione (V) as a colorless foam. $^1$H NMR ($CDCl_3$): 5.82 (vinyl H); 4.42 (7αH); 2.61 (7βH); 1.46 (t-BOC); 1.20 (19 Me); 0.92 (18 Me).

EXAMPLE 5

Preparation of $\Delta^4$-6-aza-androsten-3.17-dione (VI)

Δ4-6-t-butylcarboxy-6-aza-androsten-3,17-dione (500 mg) was dissolved in dichloromethane (10 mL) and trifluoroacetic acid (2.5 mL) was added. After stirring for 3 hours the reaction was concentrated. The residue was taken into dichloromethane and washed with 1M $NaHCO_3$, dried, filtered and concentrated to yield $\Delta^4$-6-aza-androsten-3,17-dione (VI) as a colorless solid. $^1$H NMR ($CDCl_3$): 5.09 (vinyl H), 4.8 (NH); 3.45 (7α H); 2.95 (7βH); 1.35,0.95 (18,19 Me).

EXAMPLE 6

Preparation of $\Delta^4$-6-methyl-6-aza-androsten-3,17-dione (VII)

Δ4-6-aza-androsten-3,17-dione (240 mg) was taken into DMF (10 mL) and treated with sodium hydride (75 mg, 60% in oil) and stirred 15 min. at room temperature. Methyl iodide (50 µl) was added and the mixture stirred 10 min. longer. The reaction was quenched with 1M ammonium chloride and extracted with dichloromethane. The organic solution was washed with water (x2), brine, dried over magnesium sulfate, filtered and concentrated to yield a tan solid. The solid was purified by chromatography (silica gel, $CHCl_3$:MeOH 20:1) to yield $\Delta^4$-6-methyl-6-aza-androsten-3,17-dione (VII) as a colorless solid. $^1$H NMR ($CDCl_3$): 5.09 (vinyl H); 3.35 (7αH); 2.91 (7βH); 2.8 (NMe); 1.27,0.92 (18,19 Me).

EXAMPLE 7

Preparation of $\Delta^{4,\Delta 16}$-6-methyl- 17-trifluoromethylsulfonyl-6-aza-androsten-3-one (VIII)

$\Delta^4$-6-methyl-6-aza-androsten-3,17-dione (150 mg) in THF (3 mL) at 0° C. was treated with potassium hexamethyldisilazide (1.1 mL, 0.5M in toluene). The resulting precipitate was stirred for 15 min. after which n-phenyltrifluoromethanesulfonimide (214 mg) was added forming a solution almost immediately upon addition. The amber solution was stirred at room temperature for 1 hour then diluted with EtOAc. The solution was washed with 1M ammonium chloride, water and brine, dried over sodium sulfate and concentrated. This material was purified by chromatography (silica gel, $CH_2Cl_2$: MeOH 95:5) to yield the triflate, $\Delta^{4,\Delta16}$-6-methyl- 17-trifluoromethylsulfonyl-6-aza-androsten-3-one as an amber oil (VIII). $^1$H NMR (CDCl$_3$): 5.81 (16 vinyl H), 5.61 (4 vinyl H); 4.32 (7αH); 2.59 (7βH); 1.27, 1.05 (19,18 Me).

EXAMPLE 8

Preparation of $\Delta^{4,\Delta16}$-6-methy-17-propenyl-6-aza-androsten-3-one $\Delta^{4,\Delta16}$-6-methy-17-trifluoromethylsulfonyl-6-aza-androsten-3-one (35.5 mg) in THF (1 mL) was treated with lithium chloride (10 mg), tetrakistriphenylphosphine palladium (2 mg) and allyltributyltin (0.3 mL). This solution was refluxed for 12 hours then cooled and diluted with EtOAc, washed with 10% ammonium hydroxide, water, brine, dried over anhydrous sodium sulfate, filtered and concentrated to yield a dark oil. The oil was chromatographed (silica gel, Hexanes:IPA 55:45) to yield $\Delta^4,\Delta^{16}$-6-methy-17-propenyl-6-aza-androsten-3-one (IX) as a yellow oil. $^1$H NMR (CDCl$_3$): 5.88 (21 vinyl H), 5.32 (16 vinyl H); 5.13 (4 vinyl H); 5.05 (22 vinyl H's), 2.82 (NMe), 1.3, 0.83 (19,18 Me).

EXAMPLE 9

Preparation of $\Delta^4$-6-methyl-17-propyl-6-aza-androsten-3-one (X)

A suspension of $\Delta^{4,\Delta16}$-6-methy-17-propenyl-6-aza-androsten-3-one (13 mg), EtOH (1.5 mL) and 10% Pd/C (5 mg) was stirred under a hydrogen balloon for 5 hours. The catalyst was filtered from the solution and the filtrate concentrated to give $\Delta^4$-6-methyl-17-propyl-6-aza-androsten-3-one (X) as a colorless oil. $^1$H NMR (CDCl$_3$): 5.14 (4 vinyl H); 2.81 (NMe), 1.28 (19 Me), 0.95 (22 Me); 0.81 (18 Me).

EXAMPLE 10

Preparation of $\Delta^4$-16-6-methyl-6-aza-androsten-3-one (XI)

$\Delta^{4,\Delta16}$-6-methyl-17-trifluoromethylsulfonyl-6-aza-androsten-3-one (VIII, 96 mg) in THF (2 mL) was treated with lithium chloride (65 mg), tetrakistriphenylphosphine palladium (5 mg) and tributyltin hydride (60 μl) was heated at reflux for 1 hour then cooled. EtOAc and 10% ammonium hydroxide were added and the phases separated. The organic phase was washed with water, dried over magnesium sulfate, filtered and concentrated to give an amber oil. The oil was chromatographed (silica gel, Hexanes:IPA 6:4) to yield $\Delta^{4,\Delta16}$-methyl-6-aza-androsten-3-one (XI) as a colorless oil. $^1$H NMR (CDCl$_3$): 5.89 (16 vinyl H); 5.71 (4 vinyl H); 3.3 (7α H); 2.91 (7βH); 2.81 (NMe); 1.29 (19 Me); 0.82 (18 Me). 13C NMR: 195.7 (C3); 143 (C4); 129 (C16).

EXAMPLE 11

Preparation of $\Delta^4$-6-methyl-6-aza-androsten-3-one (XII)

A suspension of $\Delta^{4,\Delta16}$-6-methyl-6-aza-androsten-3-one (17 mg), EtOH (1.5 mL) and 10% Pd/C (5 mg) was stirred under a hydrogen balloon for 5 hours. The catalyst was filtered from the solution and the filtrate concentrated to give $\Delta^4$-6-methyl-6-aza-androsten-3-one (XII) as a colorless oil. $^1$H NMR (CDCl$_3$): 5.11 (4 vinyl H); 3.35 (7αH); 2.82 (7βH); 2.78 (NMe); 1.29 (19 Me); 0.78 (18 Me). IR (CHCl$_3$) 2953, 1598, 1552, 1464,1273 cm$^{-1}$.

SCHEME V

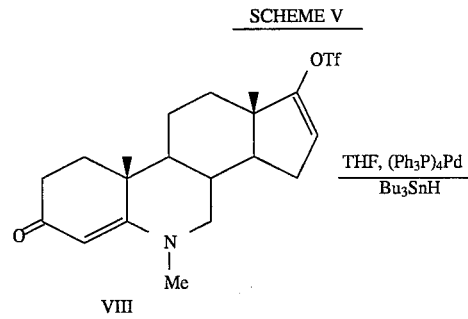

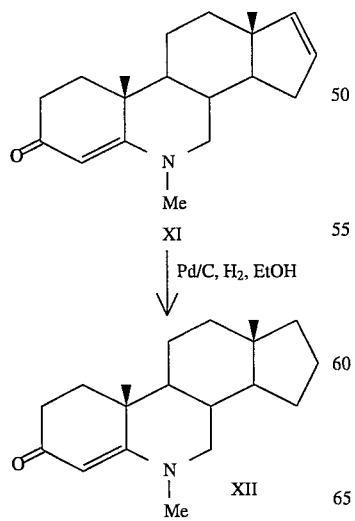

SCHEME VI

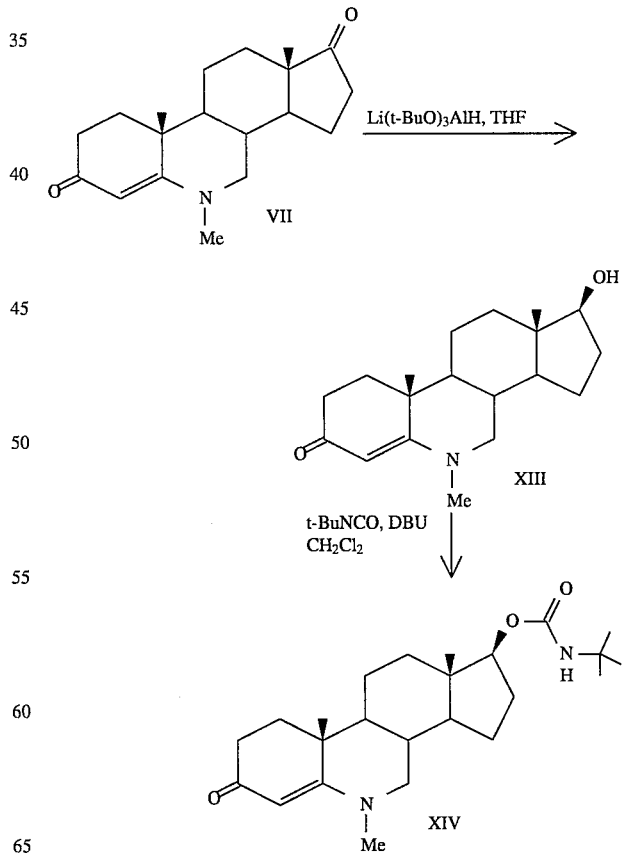

EXAMPLE 12

Preparation of $\Delta^4$-6-methyl- 17-hydroxy-6-aza-androsten-3-one (XIII)

$\Delta^4$-6-methyl-6-aza-androsten-3,17-dione (50 mg) in THF (3 mL) was chilled to 0° C. and tri-t-butoxyaluminohydride (0.18 mL, 1M in THF) was added. The reaction was stirred for 1 hour at 0° C. then quenched with 0.5M HCl until the reaction was at pH 4. The mixture was concentrated to remove the THF and the aqueous residue extracted with dichloromethane (x2). The combined extracts were washed with water, brine, dried over anhydrous magnesium sulfate, filtered and concentrated. The residue was chromatographed (silica gel, CH$_2$C12: MeOH 15:1 ) to yield $\Delta^4$-6-methyl-17-hydroxy-6-aza-androsten-3-one (XIII) as a clear glass. $^1$H NMR (CDCl$_3$): 5.31 (4 vinyl H); 3.7 (17 CH); 3.29 (7αH); 2.88 (NMe and 7βH); 1.28 (19 Me), 0.8 (18 Me).

EXAMPLE 13

Preparation of $\Delta^4$-6-methyl-17-t-butylcarbamoyloxy-6-aza-androsten-3-one (XIV)

$\Delta^4$-6-methyl- 17-hydroxy-6-aza-androsten-3-one (21 mg), dichloromethane (0.3 mL), DBU (0.1 mL) and t-butylisocyanate (0.12 mL) were stirred at room temperature for 48 hours. The reaction solution was concentrated to yield an amber oil. The residue was purified by chromatography (silica gel, CH$_2$Cl$_2$: MeOH 5:1) to yield $\Delta^4$-6-methyl-17-t-butylcarbamoyloxy-6-aza-androsten-3-one (XIV, 20 mg) as a colorless foam. $^1$H NMR (CDCl$_3$): 5.09 (4 vinyl H); 4.6 (NH); 4.51 (17 CH); 3.31 (7αH); 2.82 (7βH); 2.78 (NMe); 1.32 (t-Butyl); 1.28 (19 Me), 0.85 (18 Me).

SCHEME VII

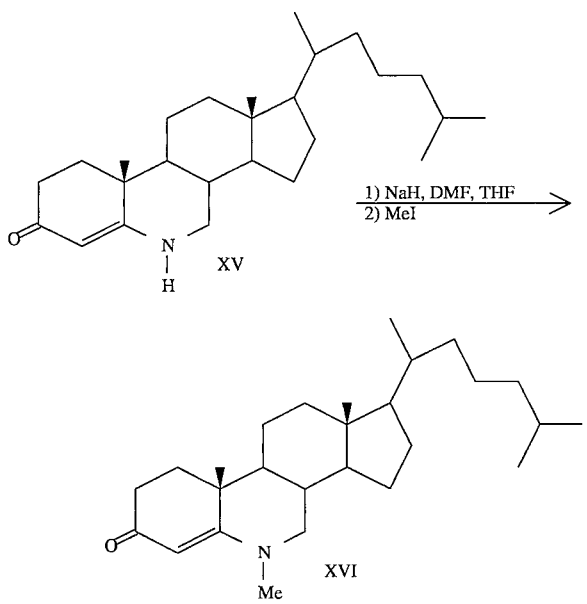

EXAMPLE 14

Preparation of $\Delta^4$-6-aza-cholesten-3-one (XV)

Starting with cholesterol (Aldrich Chemical Co.) and following the procedures in Examples 1–5 for the preparation of compound VI, $\Delta^4$-6-aza-cholesten-3-one (XV) was prepared as a colorless solid. $^1$H NMR (CDCl$_3$): 5.21 (NH); 5.09 (4 vinyl H); 3.31 (7αH); 2.82 (71βH);1.30 (19 Me); 0.94(21 Me); 0.87 (24,25 Me); 0.78 (18 Me). 13C NMR: 173.5 (C3), 114.9 (C5), 99.05 (C4).

EXAMPLE 15

Preparation of $\Delta^4$-6-methyl-6-aza-cholesten-3-one (XVI)

$\Delta^4$-6-aza-cholesten-3-one (24 mg) was taken into DMF (0.5 mL) and THF (0.5 mL) and treated with sodium hydride (5 mg, 60% in oil) and stirred 30 min. at room temperature. Methyl iodide (50 µl) was added and the mixture stirred 30 min. longer. The reaction was quenched with 1M ammonium chloride and extracted with EtOAc. The organic solution was washed with water (x2), brine, dried over magnesium sulfate, filtered and concentrated to yield a tan solid. The solid was purified by chromatography (silica gel, Hexanes:IPA, 4:1 ) to yield $\Delta^4$-6-methyl-6-aza-cholesten-3-one (XVI) as a colorless solid. $^1$H NMR (CDCl$_3$): 5.11 (4 vinyl H); 3.4 (7αH); 2.78 (7βH); 2.75 (NMe); 1.25 (19 Me); 0.92 (21 Me); 0.87 (24,25 Me); 0.72 (18 Me).

Biological Assays

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500 x g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay

The reaction mixture for the type 1 5α-reductase contained 40 mM potassium phosphate, pH 6.5, 5 mM [7-$^3$H]-testosterone, 1 mM dithiothreitol and 500 gM NADPH in a final volume of 100 µl. The reaction mixture for the type 2 5α-reductase contained 40 mM sodium citrate, pH 5.5, 0.3 mM [7-$^3$H]-testosterone, 1 mM dithiothreitol and 500 gM NADPH in a final volume of 100 µl. Typically, the assay was initiated by the addition of 50-100 µg prostatic homogenate or 75–200 µg scalp homogenate and incubated at 37° C. After 10–50 min. the reaction was quenched by extraction with 250 µl of a mixture of 70% cyclohexane: 30% ethyl acetate containing 10 µl each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min.; androstanediol, 7.6–8.0 min.; T, 9.1–9.7 min.). The HPLC system consisted of a Waters Model 680 Gradient System equipped with a Hitachi Model 655α autosampler, Applied Biosystems Model 757 -variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies s

Compounds were dissolved in 100% ethanol. The compound to be tested was pre-incubated with the enzyme (either 5α-reductase type 1 or 2) prior to initiation by addition of substrate testosterone. IC50 values represent the concentration of inhibitor required to decrease enzyme conversion of testosterone to dihydrotestosterone by 50% of the control. IC50 values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an IC50 value of about or under 100 nM.

Compounds VII, X, XII, XIII, XIV, XV, and XVI were tested in the above-described assay for 5α-reductase type 1 and type 2 inhibition, and were found to have IC50 values under about 100 nM for inhibition of the type 1 isozyme. Tested compounds of this invention that showed dual inhibitory activity additionally had IC50's under about 200 nM for inhibition of the type 2 isozyme.

The tested compounds within the scope of formula I were at least about 5 times more active in the type 15α-reductase assay than in the type 2 assay, with several being at least 10 times more active in the type 1 assay, thereby demonstrating their utility as selective type 1 inhibitors.

Human Dermal Papilla Cell Assay

The dermal papilla is a small group of cells at the base of each hair follicle, and it is presently thought that these cells are stem cells that form the basis for hair growth. These cells have been shown to have 5α reductase activity, and it is therefore possible to test inhibitors of 5α reductase in these cell culture systems.

Isolated and cultured dermal papilla cells are prepared according to the methods of Messenger, A.G., "The Culture of Dermal Papilla Cells From Human Hair Follicles," Br. J. Dermatol., 110:685–689 (1984) and Itami, S. et al., "5α-Reductase Activity In Cultured Human Dermal Papilla Cells From Beard Compared With Reticular Dermal Fibroblasts," J. Invest. Dermatol., 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min. at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800 x g for 10 min. to yield a crude nuclear pellet. The resultant supernatant is centrifuged at 10,000 x g for 15 min. to produce a crude mitochondrial pellet. The supernatant is centrifuged at 100,000 x g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 ml of the cell homogenate, in a final volume of 100 ml. Each tube contains 50–100 mg of cellular protein. Incubation is carried out at 37° C. for 30 min. During this incubation, the reaction is proportional to the time. For the study of optimum pH, titrate buffer is used at pH 4.5–6.5, and the Tris HCl buffer at pH 7.0–9.0. The protein content is determined by the method of Lowry, et al., "Protein Measurement With The Folin Phenol Reagent," J. Biol. Chem., 193:265–275 (1951).

After incubation, the reaction is stopped by adding 4 times volume of chloroform-methanol (2/1 : V/V) containing 110 mg each of carder steroids. The extracted steroids are analyzed by thin layer chromatography as previously described by Gomez, et al., "In Vitro Metabolism Of Testosterone-4-$^{14}$C and D-androstene-3, 17-dione-4-$^{14}$C In Human Skin.," Biochem., 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, MA) and unlabeled steroids can be purchased from Sigma Chemical Company (St. Louis, MO). Fetal calf serum is obtainable from Hazleton (Lenaxa, Kansas). All other chemicals are of reagent grade.

The following describes an example of methodology that can be used for detection of hair growth.

MACROPHOTOGRAPHY AND GLOBAL PHOTOGRAPHY

PROCEDURE FOR DETECTION OF HAIR GROWTH

A. Macrophotographic Procedure

Location: ID card Haircount target area

Equipment: Film: Kodak-T-max 24 exposure each of same emulsion lot number

Camera: Nikon N-6000

Lens: Nikkor 60 mm t2.8

Flashes: Nikon SB-21B Macroflash

Device: registration device

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2mm). Cut hairs are removed from the area to be photographed, using tape. Compressed air and/or ethanol wipes may also be used to facilitate removal of cut hairs.

2. Magnification: Each lens supplied has a fixed reproduction ratio of 1:1.2. Aperture: Every photograph is taken at f/22. Film: T-Max 100 (24 exposure) is used.

3. Patient's haircount target area. Three exposures (–2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E.A. and DeLong, E., J. American Academy of Dermatology, Vol. 23, p. 470 (1990).

B. Global Photographic Procedure

Locations: Color card/patient Id Global photograph

Equipment: Film: Kodachrome KR-64 24 exposure each of same emulsion lot number

Camera: Nikon N-6000

Lens: Nikkor 60 mm f2.8

Flashes: Nikon SB-23

Photographic Procedure

In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6. Aperture: Every photograph will be taken at f/11. Film: Kodachrome (24 exposure) is used.

3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is masonable.

What is claimed is:

1. A compound of the formula I

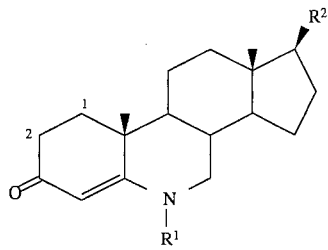

or a pharmaceutically acceptable salt thereof, wherein: R 1 is selected from -H,-CH$_3$ and-CH$_2$CH$_3$;

R$^2$ is selected from:

(1) -H, (2) -C$_{1-12}$ alkyl, (3) -C$_{1-12}$ alkyl-phenyl, (4) -O-C$_{1-12}$ alkyl or-S(O)$_n$-C$_{1-12}$ alkyl, (5) -O-phenyl or-S(O)$_n$-phenyl, (6) -C$_{1-6}$ alkyl-X-C$_{1-12}$ alkyl, and (7) -NR$^3$R$^4$, wherein R$^3$ and R$^4$ are each independently selected from -H, C$_{1-12}$ alkyl, and phenyl;

X is selected from the group consisting of O, NH and S(O)$_n$; and n is zero, 1 or 2.

2. The compound of claim 1 wherein X is selected from O and S.

3. The compound of claim 1 wherein:

R$^1$ is selected from -H and -CH$_3$; and

R$^2$ is selected from -H,-C$_{1-12}$ alkyl, -C$_{1-12}$ alkyl-phenyl, -O-C$_1$-alkyl, -O-phenyl, -S(O)$_n$-C$_{1-12}$ alkyl, and -S(O)$_n$-phenyl.

4. The compound of claim 3 wherein:

R$^1$ is selected from -H and -CH$_3$; and

R$^2$ is selected from -H,-C$_{1-12}$ alkyl, -O-C$_{1-12}$ alkyl, and-S(O)$_n$-C$_{1-12}$ alkyl.

5. The compound of claim 4 selected from:

6-methyl- 17-propyl-6-aza-androst-4-en-3-one;

6-methyl-6-aza-androst-4-en-3-one;

6-aza-cholest-4-en-3-one; and 6-methyl-6-aza-cholest-4-en-3-one.

6. A pharmaceutical composition comprising a pharmaceutically acceptable carrier and 0.01 to 1000 mg of a compound of claim 1.

7. A pharmaceutical composition comprising a pharmaceutically acceptable carrier adapted for topical application and 0.01 to 1000 mg of a compound of claim 1.

8. A pharmaceutical composition comprising a pharmaceutically acceptable carrier adapted for oral administration and 0.01 to 1000 mg of a compound of claim 1.

9. A method for treating acne vulgaris comprising the step of administering to a human subject in need of such treatment 0.01 to 1000 mg/day of a compound of claim 1.

* * * * *